US005531691A

United States Patent [19]
Shonfeld et al.

[11] Patent Number: 5,531,691
[45] Date of Patent: Jul. 2, 1996

[54] SINGLE USE SYRINGE ASSEMBLY

[75] Inventors: David Shonfeld, Great Neck; Joel S. Schoenfeld, Woodbury, both of N.Y.

[73] Assignee: Univec Inc., Garden City, N.Y.

[21] Appl. No.: 195,302

[22] Filed: Feb. 14, 1994

[51] Int. Cl.[6] ............................................. A61M 5/00
[52] U.S. Cl. ................................. 604/110; 604/187
[58] Field of Search ................................. 604/110, 187, 604/218, 220, 263, 195

[56] References Cited

U.S. PATENT DOCUMENTS

| | | |
|---|---|---|
| 4,013,073 | 3/1977 | Cunningham . |
| 4,022,206 | 5/1977 | Hilleman et al. . |
| 4,367,738 | 1/1983 | Legandre et al. . |
| 4,386,606 | 6/1983 | Tretinyak et al. . |
| 4,391,272 | 7/1983 | Staempfli . |
| 4,391,273 | 7/1983 | Chiquiar-Arias . |
| 4,731,068 | 3/1988 | Hesse ............................. 604/110 |
| 4,781,684 | 11/1988 | Trenner . |
| 4,952,206 | 8/1990 | Ibanez et al. . |
| 4,961,728 | 10/1990 | Kosinski ......................... 604/110 |
| 4,973,310 | 11/1990 | Kosinski ......................... 604/110 |
| 4,979,943 | 12/1990 | Trenner . |
| 5,000,737 | 3/1991 | Free et al. ...................... 604/110 |
| 5,021,047 | 6/1991 | Movern .......................... 604/110 |
| 5,062,833 | 11/1991 | Perler ............................. 604/110 |
| 5,067,942 | 11/1991 | Jaffee et al. . |
| 5,120,314 | 6/1992 | Greenwood .................... 604/110 |
| 5,151,088 | 9/1992 | Allison et al. . |
| 5,183,966 | 2/1993 | Movern . |
| 5,205,825 | 4/1993 | Allison et al. .................. 604/110 |
| 5,222,942 | 6/1993 | Bader ............................. 604/110 |
| 5,259,840 | 11/1993 | Boris .............................. 604/110 |
| 5,290,235 | 3/1994 | Polybank et al. . |

*Primary Examiner*—John D. Yasko
*Assistant Examiner*—Adam J. Cermak
*Attorney, Agent, or Firm*—Levisohn, Lerner, Berger & Langsam

[57] ABSTRACT

A single use syringe is provided having a rod-like plunger comprising a plurality of cylindrical ratchet teeth. A resilient locking spring dangles on the ratchet teeth of the plunger. The original location of the locking spring determines the maximum dosage which may be administered by the syringe. A first withdrawal of the plunger with respect to the barrel allows medication to be drawn into the barrel. The tab of the locking spring resiliently cams over the surface of the ratchet teeth. The locking spring is maintained in position along the barrel by outwardly directed contact points which embed into the interior side wall of the barrel. During administration of the medication, i.e., when the plunger is distally pushed with respect to the barrel, the locking spring tab cooperates with the base of the ratchet teeth and causes the spring to move along with the plunger. A second attempted withdrawal of the plunger is blocked once the locking spring has been moved to its full distal position. The thumb engaging disk of the plunger can be bent and broken off to further prevent a second use of the syringe. The disk is also useful for inventory control. The thumb engaging disk and the proximal end of the barrel mechanically cooperate as a further locking mechanism to also prevent reusability.

17 Claims, 5 Drawing Sheets

SINGLE USE SYRINGE ASSEMBLY

BACKGROUND OF THE INVENTION AND DESCRIPTION OF THE PRIOR ART

This invention relates generally to hypodermic needles and syringes, and more particularly the invention relates to a disposable, one-time or single use syringe and safety needle assembly. The safe, one-time use and subsequent disposal of hypodermic needles and syringes are immediate concerns in the medical and health professions. Accidental needle stick injuries following use of a syringe pose a significant risk to both patient, physician and nurse. The risk is a source of great anxiety due to the current HIV and hepatitis infection concerns of the general public. Thus, extreme care must be taken in the safe handling and disposal of used needles and syringes. Toward this end, the present invention represents a single use needle and syringe assembly. After the needle and syringe (hereinafter collectively referred to as a syringe) are once used, the mechanism of the present invention precludes further uses. It will, therefore, be more likely properly discarded than if further use were possible. Patient to patient cross contamination and drug user to drug user cross contamination are reduced.

The present invention is compact and, therefore, is capable of being implemented into syringes of extremely small size barrel capacity including syringes capable of administering dosages down to 1 cc. The prior art, on the other hand, as will be more fully explained hereinafter, cannot be easily and/or economically downsized while maintaining the effectiveness of the mechanisms and, therefore, they have not been commercially introduced in sizes smaller than standard 5 cc syringe bodies. The location of the locking mechanism in the prior art single use syringes enabled the device to limit the 5 cc conventional syringe to a maximum 1 cc dosage. However, it is clearly desired to have smaller maximum dosage syringes. It should be appreciated, however, that the present invention can also be adapted for use with 5 cc or other maximum dosage syringe barrels and, yet, the present invention has particular applicability to syringes of low dosage capacity.

The present invention provides a simple and inexpensive to manufacture mechanism for limiting the usage of a syringe (with or without needle) to one-time or single use only. The syringe is intended to be assembled at the manufacturing facility and provided to the physician (or nurse, patient, etc.) for use. The user fills the syringe with the appropriate medication in the conventional manner, i.e., by withdrawing the plunger with respect to the cylindrical barrel of the syringe, thereby drawing medication through the needle tip and into the barrel. Then, again, using a conventional technique, the needle is inserted to pierce the patient's skin. The plunger is manually moved with respect to the cylindrical barrel thereby forcing a piston toward the distal end of the syringe. The piston forces the medication out through the needle tip.

During the dosage administration portion of the procedure, according to the present invention, as will be more fully explained hereinafter, a locking spring travels along with the plunger shaft and, when it reaches the distal position, locking points are held against the interior sidewall of the cylindrical barrel to preclude a second retraction of the plunger with respect to the cylindrical barrel of the syringe. Thus, no further medication can be pulled into the syringe and, therefore, the syringe is incapable of being used a second time. A simple, single-use syringe is provided. The locking mechanism, precluding reuse, is automatic, i.e., it operates to block reuse without a conscious operation by the user to engage its operation.

It is also a feature of the present invention to provide the thumb-contacting portion of the syringe plunger as a break-apart disc such that, after use, the user of the syringe can simply bend or twist and remove the thumb-contacting disc and, thereby, further disable the syringe from a subsequent reuse. The ability of the thumb-contacting portion of the plunger shaft to become disengaged from the syringe also serves as a means of tracking inventory of the syringes.

It is another feature of the present invention to provide another mechanical locking device. This device, as well, blocks a second use of the syringe. It engages, however, only when the user deliberately desires to do so, by fully reciprocating the plunger to its maximum distal position. To effect this mechanical lock, the plunger and the thumb-contacting disc portion must be pushed fully toward the distal end of the syringe. When moved as described, the thumb-contacting disc portion and the plunger are locked (incapable of being withdrawn to draw in additional medication) by a male dove tail arrangement of the plunger which cooperates with a female dove tail of the barrel. Here, too, a safety mechanism is provided to prevent reuse of the syringe.

The present invention accomplishes the above objects by utilizing a new and unique plunger in association and in combination with a spring clip. The plunger comprises a plurality of cylindrical ratchet teeth. The spring clip is located by the manufacturer at a particular location on the plunger so as to limit maximum dosage of the syringe. In addition, the use of this new plunger and spring clip blocks reuse of the syringe. The construction can be incorporated into syringes of even 1 cc size without any loss of efficiency or safety.

DESCRIPTION OF THE PRIOR ART

Safety syringes have been made, in the past, which provide some degree of protection against accidental needle injury. The designs require relatively complex mechanisms, or are relatively bulky. Often, they have been relatively expensive to manufacture. All of the prior art single-use limiting mechanisms, to applicant's knowledge, are intended for use with the standard X-shaped plunger shaft of conventional syringes. The present invention, on the other hand, contemplates the use of an entirely new plunger shaft which is, in basic form, a rod comprised of cylindrical ratchet teeth. Moreover, activation of the safety features of the prior art mechanisms can sometimes fail or be intentionally disengaged. It is believed that the present invention is more effective at preventing syringe reuse.

Of particular importance, however, as mentioned, the present invention is believed extremely efficient, inexpensive and capable of being incorporated into syringes of dimensions suitable for 1 cc maximum dosage capacity. In this manner, the device can be incorporated into small dosage syringes. This is highly desirable. In contrast, prior art single use or "safety" syringes seem incapable or difficult to reduce in size. They have not been commercialized in 1 cc maximum dose capacity but, rather, the manufacturers use standard larger barrel syringes (5 cc, for example) and limit the degree of movement of the plunger shaft to limit the maximum dosage. It is a specific object of the present invention to provide a single-use syringe in a 1 cc maximum capacity.

U.S. Pat. No. 5,000,737 relates to a single use disposable syringe. The figures reveal a device adapted for placement over X-shaped conventional plunger shafts. Outwardly directed points of the claimed flute are intended to dig into the interior cylindrical sidewall or surface of the needle barrel so as to prevent movement of the disk with respect to the barrel when the plunger shaft is moved in the proximal direction (the direction for drawing medication into the barrel). Inwardly directed edges are adapted to engage the adjacent walls of the X-shaped plunger so that the device travels along with the plunger when the plunger is moved distally (to dispense the medication). FIGS. 8–16 of the identified patent relate to the claimed invention. That device is intended to be held in a quadrant of the syringe barrel defined by the X-shaped plunger member. It is described, according to the patent, as "elongated" i.e., its length from edge 36 to its base (element 50 with respect to the device shown in FIGS. 12–14) is greater than its width dimension.

The present invention, on the other hand, as will be more fully explained, is not elongated. It is compact and easily fabricated for small-sized syringes. It is less expensive to manufacture and believed far simpler to fabricate. It will not fail in the event of axial misalignment. Furthermore, the present invention contemplates use in connection with a new plunger. The locking spring as now presented is not confined within a quadrant of the barrel but, rather, it extends around the plunger on the inside of the barrel. This provides more uniform pressure of the locking mechanism against the interior sidewall of the barrel and ensures that the present invention is useful in preventing reuse of a one-time used syringe, even if the plunger is off center or out of alignment with respect to the axis of the syringe barrel. The '737 patent also shows a disc-like member which operates in a manner quite similar to the flute claimed in the '737 patent. It, too, is intended for use with conventional X-shaped plungers. It, too, seems difficult to downsize for manufacture of 1 cc syringes.

U.S. Pat. No. 5,151,088 also relates to a safety needle and syringe assembly. A disposable syringe and needle assembly is depicted and described having a small rigid retractable needle shield prodded in the syringe. Following an injection, the needle shield is extended into a locked position covering the needle. The shield only assumes the locked position when the user presses the syringe plunger past the zero volume point. Thus, if the user does not accidentally or consciously do so, this device will not block reuse. It is an object of the present invention to automatically prevent reuse of a syringe so as to eliminate person to person contamination, a consequence of needle reuse. Automatic engagement of the locking mechanism is not accomplished by the '088 device. Utilizing the invention of the '088 patent, however, a user, desiring to defeat the mechanism and to reuse the syringe, can avoid engagement of the locking mechanism by deliberately failing to press the syringe plunger past the zero volume point.

U.S. Pat. No. 5,205,825 (Ellison et al.) relates to an insertable element for preventing reuse of plastic syringes. This device, similar to that shown in the Free et. al. '737 patent, provides a locking mechanism intended to be retrofitted into existing conventional syringes by inserting the same onto the standard X-shaped plunger within a plastic cylindrical barrel of the syringe. The same comments previously made with respect to the device of the Free et. al. patent are equally applicable to the Ellison et. al. patent i.e., with respect to its inability to b,e made effectively and efficiently in a smaller maximum dose syringe and, further, the problem of misalignment of the X-shaped plunger visa vis the cylindrical barrel.

U.S. Pat. No. 5,067,942 relates to a single-use hypodermic needle, as well. When the needle assembly and the syringe are assembled, two separable tabs held within a basket force the sheath to retract and expose the port in the needle whereby a fluid can flow through the needle. Upon disassembly of the needle syringe, the tabs separate from the basket and are effectively destroyed for further use in retracting the sheath. The present invention is believed far simpler, less expensive to manufacture, automatic and is more easily adapted for smaller sized syringes then that shown in the '942 patent.

A number of safety syringe designs incorporating needle covers have also been proposed. U.S. Pat. Nos. 4,909,791 and 4,982,842 employ jaw members pivotally mounted onto a syringe barrel for covering a needle after use.

U.S. Pat. No. 4,969,877 discloses a syringe assembly in which an outer casing is provided around an inner chamber or syringe portion which slides on the outer casing to an operational position and to a retracted position at the forward and rearward ends of the outer casing, respectively.

Another prior art device which has dealt with the problem of reusable syringes is U.S. Pat. No. 2,618,263. That patent discloses a pre-measured medication in an ampule adjacent to the inner end of a needle. Upon pressure being applied to the ampule, the needle penetrates the ampule and the medication is discharged. The entire device is then intended to be disposed.

U.S. Pat. No. 4,013,073 discloses a collapsible single-use syringe wherein the interior of the collapsible wall is constructed such that when the walls are pressed together to discharge the medication, they interlock and therefore render the device incapable for reuse.

U.S. Pat. No. 4,022,206 shows a method and apparatus for storing and delivering a vaccine in a single dose prepackaged system. No provision is made for rendering the unit mechanically incapable for subsequent use.

U.S. Pat. No. 4,391,273 shows a rigid type syringe including a pin which is attached to the piston which penetrates the bottom wall of the cylinder after the injection has been completed. This, too, renders the syringe inoperable after a first time use. In an alternative embodiment, the patent shows a knife blade which permits movement of the cylinder in a forward direction but the knife serves to cut the sidewall of the cylinder if there is an attempt to recycle the piston or reuse the syringe.

Prior techniques for preventing reuse of needle syringes include various arrangements for locking out the plunger of the syringe after it has been first loaded and then reciprocated to the end of its travel to inject the contents of the syringe. For example, U.S. Pat. No. 4,731,068 discloses a two-part lock construction having a band or sleeve assembled at the injection end of the syringe and dimensioned to be frictionally slidable along the inner wall of the syringe. A spider-like element is mounted in a fixed position on the plunger and has barbed points engaged with the sleeve. When the plunger is first retracted, the spider element and sleeve travel toward the end of the syringe, together with the plunger. When the plunger is depressed toward the injection end, the sleeve remains at the distal end (through frictional engagement with the inner wall) while the spider element travels toward the injection end with the plunger. If a second attempt is made to retract the plunger, the barbs of the spider element, now exposed to the inner wall in the absence of the sleeve, will engage the inner wall of the syringe and prevent a second retraction.

An alternative embodiment shown in the '068 patent has the sleeve slidably supported on the plunger and engaged with the spider element. That element is provided with curved spring-like prongs assembled at the distal end of the syringe. On the first retraction, the sleeve remains engaged with the spider element, and on the first depression, it is moved toward the injection end to expose the prongs of the spider element. An attempt to retract the plunger a second time will be prevented by engagement of the prongs with the plunger. Other devices, for example, U.S. Pat. Nos. 4,781,684; 4,493,703; 4,391,272 and 4,367,738 provide modifications to the plunger or syringe wall structure. These allow only one way movement of the plunger or lock or disable the plunger after a first depression. They, too, relate to single use syringes.

The present invention is extremely easy to fabricate, manufacture and assemble. It is easily capable of use with standard size syringe barrels and, in addition, of commercial importance, it is fully capable of being down-sized for use in connection with syringes having a maximum dosage capacity of 1 cc. The present invention is fail-safe, i.e., automatic in operation and, in the preferred embodiment, as will be more fully explained, provides multiple lock-out mechanisms thereby ensuring that re-use of a one-time used syringe can not occur. The present invention, furthermore, allows for the selective location of the locking spring mechanism on the cylindrical plunger shaft such that maximum dosages can be provided by the manufacturer even though the syringe barrel can be manufactured in a single large capacity, i.e., a standard 5 cc size. Thus, location of the locking spring mechanism with respect to the barrel and the plunger, at the time of manufacture, ensures that the administering physician, nurse, technician or user can not administer an overdose of the particular medication. The locking spring mechanism can assume a variety of initial locations at the time of manufacture, so that there can be economy of manufacture since only one large, cylindrical barrel and plunger element need to be manufactured. The position of original location of the locking spring mechanism with respect to the plunger determines the maximum quantity of dosage which a particular syringe is capable of administering. Thus, the present invention not only provides a mechanism for ensuring that syringes can not be reused, but, in addition, the locking spring mechanism limits the amount of medication which can be administered for any particular use of that syringe.

The present invention, as will be more fully detailed hereinafter, also provides for a back-up safety mechanism to further disable the syringe after its first time use. This feature however, is not automatic but, rather, requires that the user physically separate the thumb-contacting disc portion of the plunger from the plunger shaft to thereby further mechanically disable the syringe from being used a second time. Removal of the thumb-contacting disc portion serves a secondary purpose of facilitating inventory control since the discs, the remaining portion of the syringe after the bulk has been discarded, can be used to facilitate inventory control.

It is a further object of the present invention to provide yet another lock-out feature preventing the syringe from being used a second time. In this embodiment, a full distal reciprocation of the plunger with respect to the syringe barrel will cause a male dove-tail portion of the thumb-contacting disc to engage and mechanically lock into a female dovetail like arrangement of the cylindrical barrel. This locks the disc and shaft fully within the interior of the barrel and prevents movement of the shaft outwardly with respect to the barrel. Blockage of this movement prevents further medication from being withdrawn into the body of the syringe, thereby rendering the device unreusable.

SUMMARY OF THE INVENTION

The present invention relates to a single use syringe wherein re-use is mechanically blocked. It is an object of the present invention to provide a single use syringe which is simple in construction, inexpensive to manufacture and automatically prevents re-use. It is a further object of the present invention to provide an inexpensive syringe which is capable of mechanically blocking re-use which syringe can be made of small dosage capacity. For example, it is a specific object of the present invention to provide a one-time use syringe capable of maximum dosage or capacity of no more than 1 cc.

Another object of the present invention is to provide an inexpensive, spring-like mechanism which, when placed around a cylindrical ratcheted plunger shaft, limits the quantity of medication which can be withdrawn into the barrel of the syringe and then administered. The initial location of the locking spring mechanism, with respect to the ratcheted cylindrical shaft, determines the maximum capacity of that particular syringe. Thus, it is a specific object of the present invention to provide a single use syringe capable of having a variety of maximum dosage capacities dependent upon the location of the spring clip with respect to the plunger shaft. The manufacture of a single size barrel, therefore, provides for economies of manufacture.

It is a further object of the present invention to ensure that a one-time use syringe is provided which can not be easily intentionally disabled. It is also an object of the invention to ensure a one time syringe even in the face of misalignment between the plunger and the axis of the barrel of the syringe. This is, in part, accomplished by the use of a new plunger shaft which is basically rod-like and cylindrical, not of X-shape configuration, and by use of a surrounding, spring-like clip locatable around the cylindrical shaft. In this manner, non-axial alignment between the cylindrical plunger shaft and the inside barrel wall of the syringe will not disable the one-time use locking mechanism. It is a specific object of the present invention to provide a one-time use locking mechanism for a disposable syringe which is capable of use on plunger shafts which are not of the conventional or X-shape configuration. Eliminating the X-shaped plunger allows the present invention to be more easily made in smaller dimensions.

The plunger shaft of the present invention comprises a plurality of cylindrical ratchet teeth. The locking spring, as will be explained, is intended to be initially located on a selected one tooth of the plunger. Thus, the present invention allows for more precise dosage limiting than available with the prior art devices. A mechanical locking between the locking spring and the plunger ensures the maximum dosage in fixed integral amounts whereas the prior art controls maximum dosage by sliding location of a flute along the X-shaped legs of the plunger, not nearly as easy to precisely control.

It is a further object of the present invention to provide a thumb contacting disc portion of the plunger shaft which can be selectively bent or twisted and removed from the plunger shaft after the syringe has been used. In this manner, the thumb-contacting disc portion can be used for keeping track of syringe usage and inventory. Furthermore, removal of the thumb-contacting disc portion of the plunger shaft serves to further disable the syringe, preventing possible re-use.

It is a further object of the present invention to provide another locking mechanism further disabling the syringe from re-use after a one-time intended use. This locking mechanism is accomplished by cooperation of a male dove tail of the thumb-contacting disc portion of the plunger shaft with a female dovetail-like receptacle at the proximal end of the barrel of the syringe. A full reciprocating cycle of the plunger shaft with respect to the cylindrical barrel of the syringe serves to mechanically lock the plunger shaft into its full distal position thereby preventing a second unauthorized or unintended withdrawal of the plunger shaft with respect to the barrel of the syringe.

Another object of the present invention is to provide a mechanism whereby syringes of identical dimensions can be restricted to contain and deliver different dosages, thereby reducing the need for syringes of different sizes.

The objects, features and advantages of the present invention will become apparent from the following detailed description of the preferred embodiment of the invention considered in conjunction with the drawings, as follows:

DETAILED DESCRIPTION OF THE DRAWINGS AND THE PREFERRED EMBODIMENT

Figure 1:
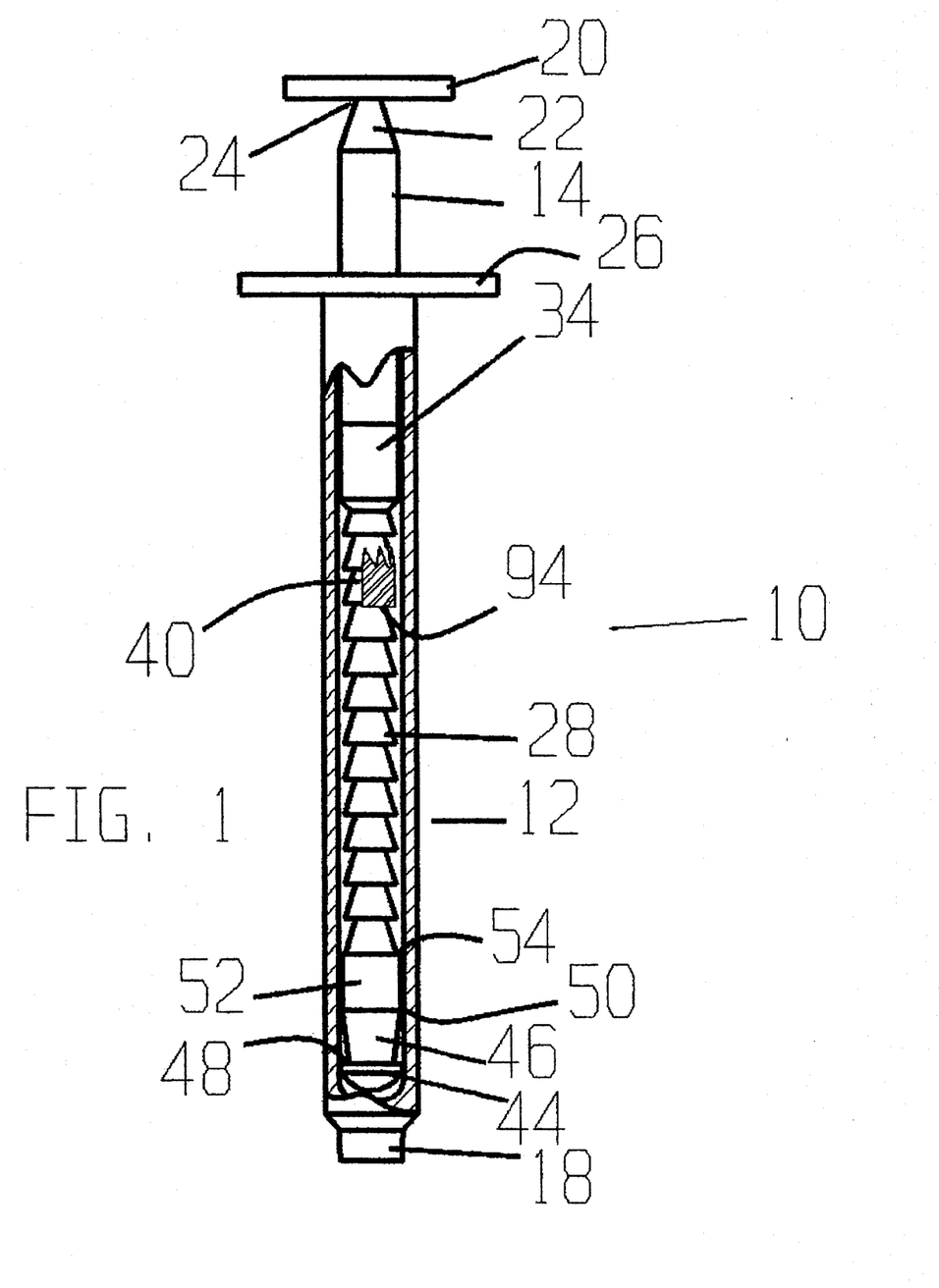
FIG. 1 is a side plan view of the syringe portion of the present invention showing the locking spring in its initial position, as sold by a manufacturer, encircling the cylindrical plunger shaft. This Figure shows the syringe of the present invention in its configuration as intended to be distributed to a user for first filling with medication and then subsequent dispensing of the same. The Figure does not show the needle of the syringe. The needle is conventional in configuration. Description is not considered necessary. It is intended and anticipated that the syringe will be sold along with a suitable needle.
Figure 3:
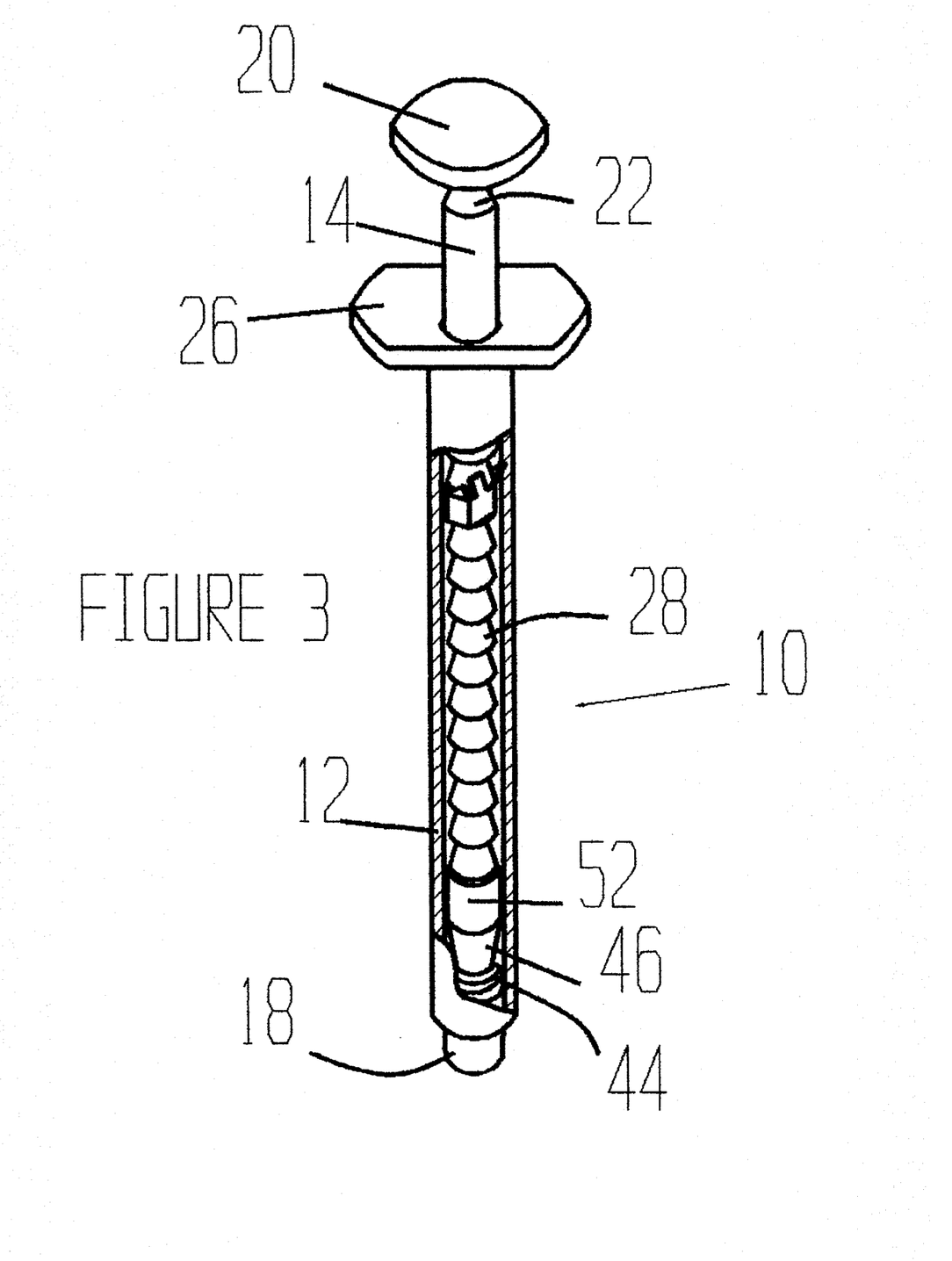
FIG. 3 is an isometric or perspective view of the device shown in FIG. 1.

As best seen in FIGS. 1 and 3, the present invention, a syringe 10, comprises a main cylinder body 12 and a reciprocating plunger member 14 slidable, received and contained within the cylinder body 12. A needle is not illustrated but it is anticipated that the syringe 10 will be sold integral with a needle, as is currently conventional. Of course, the syringe can be sold separately from the needle. The details of the construction of the needle are not believed necessary for a full understanding and appreciation of the present invention. The needle is secured to the tip 18 of the cylinder body 12. For purposes of this description, the end of the cylinder body 12 having the tip will be referred to as the distal end and direction or motion toward that end is referred to as distal. The other end, i.e., the end of the plunger member 14 having the thumb-contacting disc 20 is referred to as the proximal end and direction or motion toward that end is referred to as proximal. As can be seen in FIGS. 1 and 3, the thumb-contacting disc 20 is secured to the proximal end of the plunger member 14 and facilitates withdrawal of the plunger member 14 with respect to cylinder body 12 as well as reciprocating or distal movement of the plunger member 14 toward the tip 18 of the cylinder body 12. The distal motion dispenses medication, held in the barrel, through the tip 18 and the needle. The medication is dispensed from the cylinder body or barrel by the sliding action of piston 44 against the sidewall of the barrel.

The thumb-contacting disc 20 is secured to frusto-conical segment 22 of the plunger member 14. The smaller diameter end of segment 22 forms the base 24 for the thumb-contacting disc 20. After use of the syringe the thumb-contacting disc 20 can be bent with respect to the base 24 until the disc breaks apart or separates at that line of fracture. Removal of the thumb-contacting disc 20 facilitates further disabling of the syringe, after use, ensuring that the syringe Can not be used again since it would be difficult to reciprocate the plunger without the disc 20. The disc 20 serves not only to disable the syringe from further reuse, but also as a convenient, compact inventory control.

The cylinder body 12 is provided, at its proximal end, with a finger grip 26. It facilitates the reciprocation of the plunger member 14 with respect to cylinder body 12 and provides a convenient rest and support surface for the user's fingers during use.

The plunger member 14 is a rod, in basic configuration. Frusto-conical ratcheting teeth 28 extend over a significant portion of the length of the plunger member 14. As can be best seen in FIG. 2, each ratchet tooth 30 comprises an inclined, outwardly extending (from top to bottom) camming or inclined surface 98, and is secured to an adjacent ratchet tooth by a base or common plane 32 having an enlarged diameter D1 (for the upper relative tooth) and a reduced diameter D2 (for the lower relative tooth).

Figure 2:
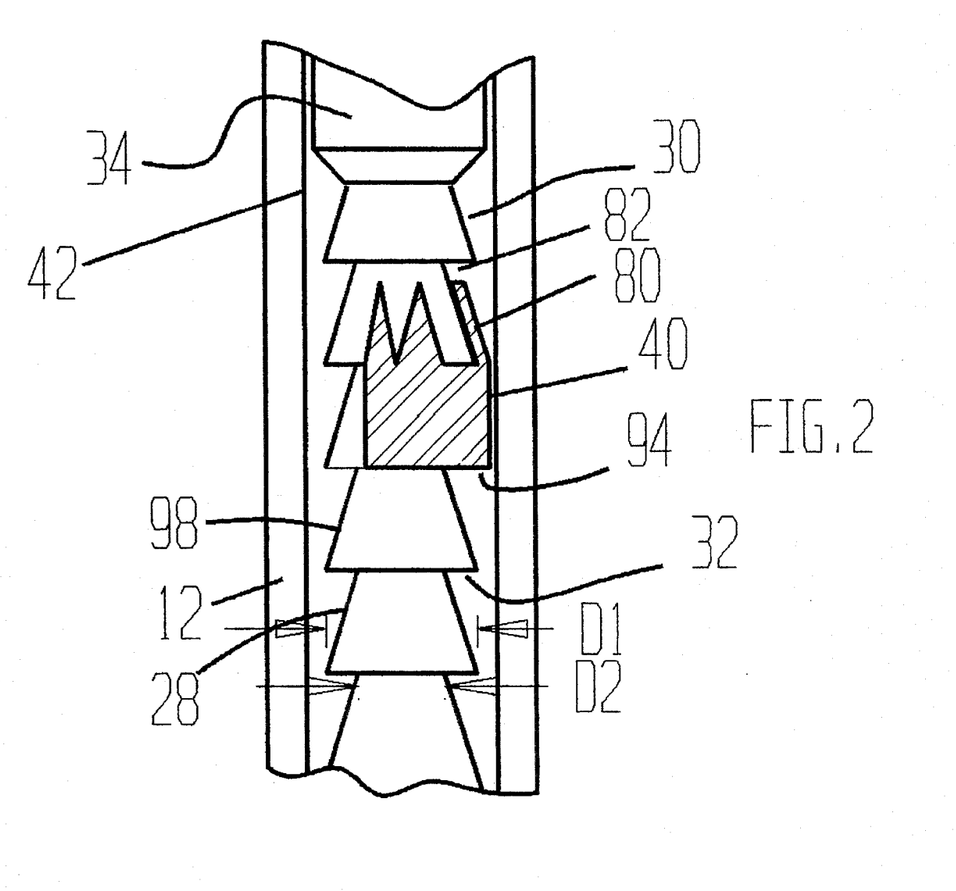
FIG. 2 is an enlarged, partial side plan view showing the mechanical locking; spring or clip of the present invention, as installed around the ratchet-toothed cylindrical plunger, located within the barrel of the syringe.

A plunger seal 34 encircles plunger member 14 directly above the most proximal ratchet tooth (best seen in FIGS. 1 and 2). The plunger seal 34 can be integrally molded or formed with the plunger or, alternatively, it can be a separate rubber component. The plunger seal has an outside diameter larger than the diameter D1 of the ratchet teeth and, in one embodiment, the plunger seal has a diameter about that of the interior sidewall barrel. The plunger seal provides a barrier between the outside of the syringe and the ratchet teeth so that air and/or other foreign objects cannot enter between the plunger member 14 and the interior sidewall of the cylinder body 12. Thus, the plunger seal 34 serves as a sealing device to prevent unauthorized access to the locking spring 40 so that it can not be disabled from its intended use. In the alternate embodiment, the plunger seal 34 is rubber and physically contacts and is, at least in part, partially compressed by the relative diameter of the interior cylindrical sidewall 42 in comparison to the diameter of the plunger seal 34.

The distal end of the plunger member 14 comprises a piston or fluid-pushing sealing member 44. It is preferably made from a rubber-like substance, partially compressible material. Here, again, the piston 44 may be integrally molded or formed with the plunger or a separate component. The piston 44 has a diameter, when compressed, substantially equal to the diameter of the interior sidewall 42 and provides a sliding yet sealing contact therebetween. When the plunger member 14 is reciprocated within the cylinder body 12, all fluid (distal of the sealing member 44) will be pushed through the tip 18 and, therefore, through the needle 16 (not shown). The sealing member 44 also prevents any medication or fluid from entering into the cavity above (or proximal) to the piston 44. Piston 44, of course, travels along with the plunger member 14 and is physically secured thereto.

Connected to the proximal end of the piston 44 is an enlarged frusto-conical extended section 46 having its reduced diameter portion 48 secured to the proximal side of piston 44 and the enlarged diameter portion 50 extending upwardly or proximally along the plunger. The proximal side of extended section 46 is provided with seal section 52 which, similar to plunger seal 34, provides a safety seal to prevent unauthorized access to the ratchet teeth 28 and the locking spring 40. It, too, prevents a paper clip, a knife point, etc. from gaining access into the space proximal of extended section 46. The diameter of section 52 is about that of the interior sidewall of the cylinder body 12.

Figure 4:
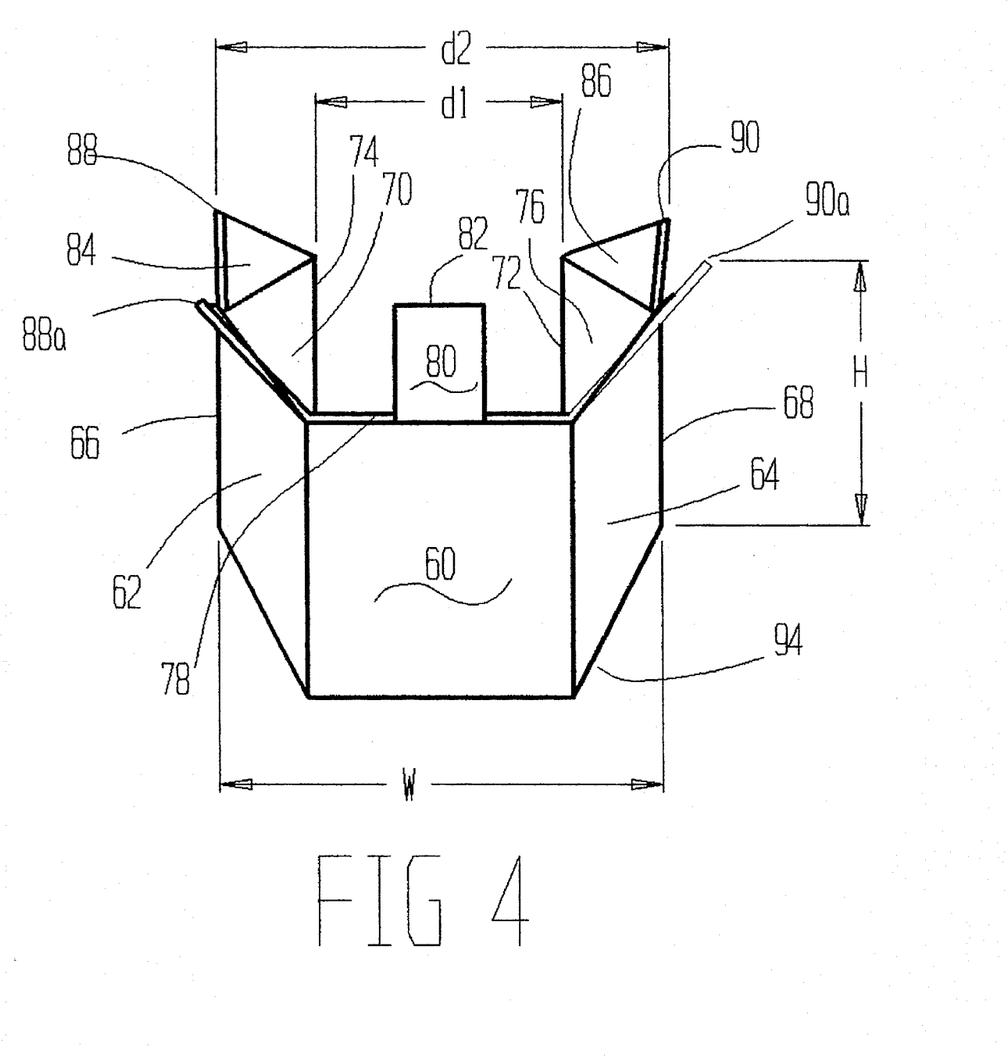
FIG. 4 is an enlarged perspective view showing the locking spring or clip of the present invention.

The locking spring 40 is best seen in FIGS. 1, 2 and 4. Its basic configuration is that of a hollow one-side open hexagon. Preferably, the spring is formed from a thin piece of metal. The material must be at least partially resilient such that it can be spread apart (by the manufacturer) for initial placement around the particular selected ratchet tooth 30 and, yet, after placement on the plunger member, the locking spring 40 springs back toward its original dimensions and configuration. The resiliency allows the locking spring 40 to be secured about the plunger member by pressing it over a ratchet tooth, spreading its front walls 70 and 72 and, yet, after initial placement, the spring member can not become dislodged. The dimensioning of the locking spring 40 is such that the distance d1 (see FIG. 4) is less than the diameter D1 of the base 32 of the ratchet teeth. It will be appreciated that the locking spring 40 extends about, at least 180 degrees of the plunger member 14 such that, after placement, it can not accidentally fall off the plunger member. In the preferred embodiment of the invention, the height h of the locking spring 40 is less than the overall width W. In this manner the locking spring is more disc-like and is not elongated. It is thus easier and less expensive to manufacture than an elongated device because it requires less material and can be made with high speed manufacturing apparatus. The drawings illustrate the locking spring as extending over about 3 ratchet teeth (See FIG. 2) for ease of illustration only. In actual manufacture, however, the height of the locking spring can be less.

The locking spring has a flat back section 60 and a pair of opposed, outwardly extending sidewalls 62 and 64, secured to the side edges of the back section. Extending inwardly from the outermost edges 66 and 68 of sidewalls 62 and 64, respectively, are front walls 70 and 72. Each of the walls— back section 60 sidewalls 62 and 64, front walls 70 and 72 are of rectangular configuration. The leading edges 74 and 76 of front walls 70 and 72, respectively, are separated by a distance d1 which, as mentioned, is less than the diameter D1 of the base 32 of ratchet teeth 28. In this manner, as mentioned, the locking spring 40 can expand outwardly over and around the ratchet tooth 30 and, yet, as the leading edges 74 and 76 pass by the maximum diameter D1 of the base 32 of the plunger, the resiliency of the locking spring forces it to assume its original dimensions. In this manner, the, spring will not accidentally fall off or be removed from the plunger member unless physical force is deliberately applied thereto.

The top edge 78 extends along back section 60. Extending inwardly and upwardly from top edge 78, basically centered along back section 60, is a tooth-engaging tab 80. Tab 80 is rectangular and has a top edge 82 which, as illustrated in FIG. 2, is configured to abut (as later described) against the bottom of the base 32 of a ratchet tooth 30 beneath which the locking spring 40 is originally located. Thus, it should be appreciated that top edge 82 extends inwardly from back section 60 a sufficient distance so that the locking spring 40 will not slide distally over a ratchet tooth onto another ratchet tooth but, rather, top edge 82 will initially rest on inclined surface or camming surface 98. The locking spring 40 is prevented from proximal movement with respect to the plunger by the top edge 82 abutting beneath base 32. It should also be understood that movement of plunger 14 in the distal direction forces the locking spring to move with it since base 32 pushes on top edge 82. However, the resiliency of locking spring 40 and, specifically, tab 80 allows for the plunger to move proximally with respect to the held-in-position or stationary locking spring since the tab 80 will cam over inclined surfaces 98.

Extending upwardly and outwardly from the top edge of side walls 62 and 64, as well as from front walls 70 and 72 are locking teeth. Locking teeth 84 and 86 extend from front walls 70 and 72, respectively, and are clearly shown in FIG. 4. These locking teeth are preferably of triangular configuration and terminate in contact points 88 and 90. The contact points 88a and 90a of the other locking teeth for the side walls 62 and 64 are, of course, similar to those shown in FIG. 4. Contact points 88, 90, 88a and 90a extend outwardly from the outside planar surface of front walls 70 and 72 and sidewalls 62 and 64 and, indeed, the locking points contact the interior sidewall 42 of the cylinder body 12. They bear against the sidewall. The hardness of contact points 88, 88a, 90a and 90 is greater than the hardness of the interior sidewall of the cylinder body 12 such that the contact points will dig into the interior sidewall surface of the cylinder body when the locking spring is sought to be carried by the plunger in the proximal direction. When such movement is attempted, the contact points prevent the locking spring from moving proximally. The locking spring can, however, move distally since the contact points will slide over the interior sidewall in the distal direction. The shape and resiliency of the device, however, forces the contact points to dig into the sidewall. When the plunger is moved distally, the locking spring will move along with it since the contact points will slide along the interior sidewall in one direction but they dig into the sidewall when movement is attempted in the other direction. The distance d2 (See FIG. 4) between contact points 88 and 90 may be less than the interior sidewall diameter of the cylinder body 12, and, yet, since the contact points 88, 88a, 90a, and 90 extend outwardly with respect to the outside planar surface of the front walls 70 and 72 and sidewalls 62 and 64, all contact points 88, 88a, 90a and 90 are expected to contact the interior sidewall 42 of the cylinder body 12. Geometry dictates that the distance between the center point of locking spring 40 to the contact points is greater, when the spring is not compressed by the interior sidewall than the internal radius of the interior sidewall. In an alternate embodiment two or more locking springs can be located on multiple ratchet teeth of the plunger rod.

The construction, manufacture and use of the device is as follows: The cylinder body 12 is formed in the same manner and with the same materials as is currently done in connection with conventional syringes. The plunger member 14, with its ratchet: teeth, piston and seals 44, 52 and 34, is preferably formed as a single plastic molded product. The manufacturer determines the maximum dosage for a particular batch of syringes. With that maximum dosage in mind, the locking spring 40 will be placed (pressed) around the ratchet tooth which corresponds to the maximum desired dosage. This is accomplished by spreading front walls 70 and 72 camming edges 74 and 76 over base 32. The individual ratchet teeth can be marked or imprinted during molding with suitable identifying indicia to facilitate the location of the locking spring 40 about the particular ratchet tooth which corresponds to a particular maximum dosage. Locating the locking spring 40 toward the distal end of the plunger member 14 provides a smaller maximum dosage for the syringe than locating the same spring member 40 toward the proximal end. The locking spring 40 is positioned about plunger member 14 such that leading edges 74 and 76 cam around a base 32. In this manner, the edges 74 and 76 of the locking spring physically spread such that dimension d1 becomes greater than the diameter D1 of the base 32 of the ratchet teeth. Then, when the leading edges pass the diameter D1 of the plunger member, the resiliency of the locking spring forces the leading edges 74 and 76 to once again assume dimension D1. In this manner, it should be appreciated by those of ordinary skill in the art that the locking spring 40 is located around the plunger member such that the locking spring cannot be easily removed without applying physical force to once again spread apart leading edges 74 and 76. The locking spring is held on the plunger by the 180°+configuration and by the tab 80 resting on the inclined surface 98 of the ratchet tooth. Thus, the locking spring does not grip a ratchet tooth but is loosely held onto the ratchet tooth. Top edge 82 of tab 80 is, as mentioned, projected or bent inwardly a sufficient distance such that it bears against the cam surface 98, the incline of a particular ratchet tooth, since the maximum radius of the ratchet tooth, at base 32, is greater than the distance defined by the center of the locking spring to top edge 82. The locking spring "dangles" on an inclined surface 98 of the particular ratchet tooth onto which it is secured although the contact points of the spring clip, when the spring clip and plunger are inserted into the barrel, physically contact the inside wall of the barrel and thus, to some extent secure the locking spring on the inclined surface 98.

Locking spring 40 can not move proximally with respect to the plunger member 14 since that relative movement is blocked by the mechanical interaction of the tab 80 to the base of the upwardly adjacent ratchet tooth. With the locking spring located at the position desired, the manufacturer completes the assembly process by securing the plunger member 14 along with the locking spring 40 into the cylinder body or barrel. The article is then packaged and delivered to the end user.

Upon receipt by the user, the syringe 10 is removed from its packaging. In a conventional manner, the needle 16 is inserted into the vial of medication and the thumb-contacting disc 20 moved proximally with respect to finger grip 26. During plunger retraction, locking spring 40 will remain fixed in the barrel. The plunger can proximally move until the uppermost seal element 54 of seal 52 contacts the bottom edge 94 of the locking spring 40. Once this abutment occurs, further proximal movement of the plunger member 14 can not occur since the contact points of the locking teeth are physically dug into the interior sidewall 42 of the cylinder body 12 (precluding proximal locking ring movement) and the seal element 54 abuts against the locking spring. It should be appreciated by those of ordinary skill in the art that the locking spring 40 cannot move when the plunger member 14 is proximally moved. The contact points prevent proximal movement of the locking spring. Initial location of the locking spring and thus locking teeth 84 and 86 with respect to the plunger determines the maximum amount of relative reciprocation of the elements and thus the maximum dosage which can be administered by the syringe. During proximal plunger movement, the tab 80 of the locking spring glides or cams over the incline surfaces 98 of the ratchet. As plunger member 14 is withdrawn or moved proximally with respect to cylinder body 12, the resiliency of the tab 80 of locking spring 40 is such that top edge 82 will travel over each inclined surface 98 of each ratchet tooth 30. Since the locking spring is maintained within the cylinder body 12 in relative position by the interaction of the locking points 88, 88a, 90a and 90 against the inside cylindrical surface of the cylinder body 12, the plunger member 14 can be fully withdrawn until uppermost seal 54 contacts the bottom edge 94 of the locking spring 40. When this occurs, however, further proximal movement of the plunger member 14 is blocked since further desired movement of the plunger member 14 will only further embed the locking points 88, 88a, 90a and 90 into the inside cylindrical wall 42 of the cylinder body 12. Thus, the plunger member is restricted by its relative movement with respect to the cylinder body. However, as mentioned, the top edge 82 of tab 80 cams over each of the inclined surfaces 98 of the individual ratchet teeth.

With the medication now contained within the cylinder body 12, more specifically, between piston 44 and the tip 18 of cylinder body 12, the user is ready to dispense the medication, as and when desired. The needle is inserted through the patient's skin and the user then applies pressure onto thumb-contacting disc 20 such that plunger member 14 is moved distally, thereby pushing piston 44 distally and, thereby, dispensing all medication through tip 18 and needle 16. Since top edge 82 of tab 80 will be pushed distally by contact with the base 32 of the above-located ratchet tooth, the locking spring 40 will slide distally within the barrel, as plunger member 14 is distally moved to dispense medication. The contact points only prevent proximal movement of the locking spring; distal movement is allowed by the sliding of the contact points along the interior sidewall.

After all medication has been dispensed from the syringe, a second reciprocation of the plunger member 14 with respect to cylinder body 12 is mechanically blocked since locking spring 40 is now located adjacent to the seal 54. Here it is prevented from a second proximal movement by contact points 88, 88a, 90a and 90 digging into the interior sidewall 42 of the cylinder body 12 and the abutment between edge 94 and seal 54. Thus, it should be apparent, that a second reciprocation, to draw medication or drugs into the syringe 10, is mechanically blocked since the plunger member 14 cannot move a second time in the proximal direction with respect to cylinder body 12.

To further disable the syringe 10 for subsequent potential use, the user can, if desired, bend or twist the thumb-contacting disc 20 along the line of fracture, at 24, until it breaks apart. Without the thumb-contacting disc 20 secured to the plunger member 14, it is far more difficult to reciprocate the plunger member 14, in either direction, even assuming that one could first disable the locking spring mechanism. Furthermore, the thumb-contacting disc 20 can now serve as a means to limit syringe distribution; for example, a certain number of such discs may be collected and turned into the manufacturer or dispenser in exchange for a like number of new syringes.

Figure 5:
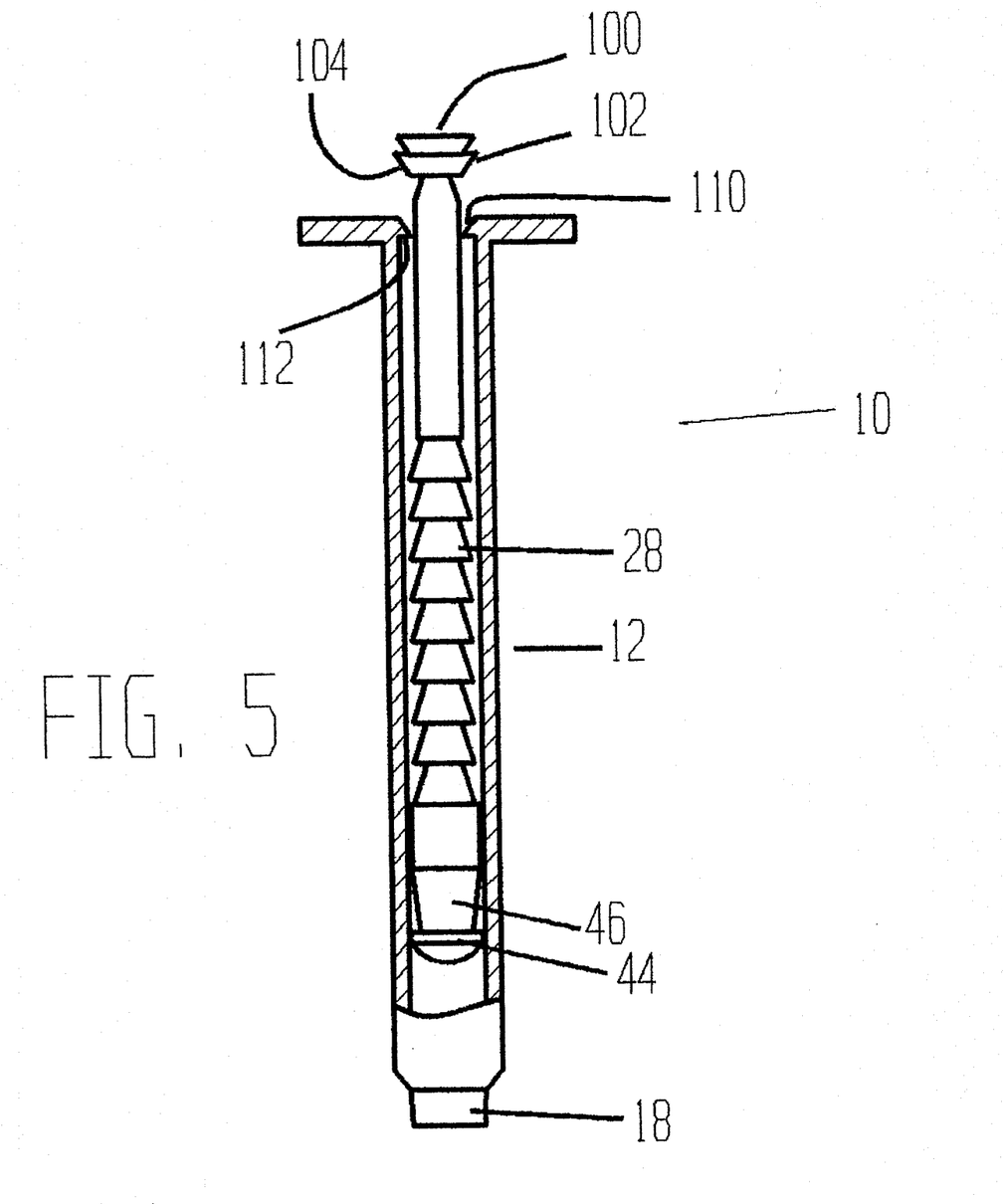
FIG. 5 is a side cross-sectional view of an alternate embodiment of the barrel and thumb-engaging disc portion of the plunger.

In an alternate embodiment of the present invention, thumb-contacting disc 20 is provided (see FIG. 5) with an inclined thumb section 100, and a second, inclined outerwall disc-like section 102. Together these comprise a male dovelike arrangement for the plunger. The proximal portion of the cylinder body 12 is provided with an annular inwardly directed edge 110, terminating in a locking lip 112. Together these comprise a female, dove-tail like arrangement for the barrel. Thus, when the thumb-contacting disc 20 is fully reciprocated in the distal direction, edge 104 slides on edge 110 to separate the barrel until the locking lip 112 of the cylindrical body 12 will overlap the second annular disc-like section 102, thereby preventing any further proximal or distal movement of the plunger with respect to the cylinder body 12. Thus, it should be appreciated and apparent to those of ordinary skill in the art that the smallest diameter of the edge 110, at the point of locking lip 112, is less than the largest diameter of edge surface 104, although the resiliency of the barrel allows edge 110 to cam over edge 104 until held by locking lip 112.

There has been described several embodiments of a single use hypodermic needle and syringe assembly., While the invention has been described with reference to specific embodiments, the description is illustrative of the invention and is not to be construed as limiting the invention. Various modifications and applications may occur to those skilled in the art without departing from the true spirit and scope of the invention.

I claim:

1. A single use syringe comprising:

a hollow barrel having an interior cylindrical side wall, a hub for a needle tip at the distal end of said barrel and a proximal end opposite to said hub for a needle tip end of said barrel;

a plunger rod having a longitudinal axis located within said barrel for axial movement therein for drawing fluid into and expelling fluid out of said barrel through said hub for a needle tip, said plunger rod extending beyond said barrel at said proximal end and having a sealing piston at said hub for a needle tip end;

said plunger rod comprised of two or more ratchet teeth extending along said longitudinal axis;

an open-ended resilient locking spring, locatable on any one of said ratchet teeth, said locking spring extending around the circumference of said plunger rod by more than about 180 degrees but less than 360°, said locking spring having at least one inwardly directed, ratchet tooth-engaging tab and at least one, outwardly-directed contact point;

said plunger rod being free to move a first time toward the proximal end of said barrel, said tab camming over the surface of said ratchet teeth as said plunger rod moves proximally while said locking spring is held in position by the frictional engagement of said contact point against said interior cylindrical sidewall and, yet, distal movement of said plunger rod causes said tab to engage the base of one of said ratchet teeth such that said locking spring moves along with said plunger rod in said distal direction;

whereby said locking spring permits the syringe to be loaded with medication in the volume of said barrel defined by the predetermined location of said locking spring on said plunger rod and by proximal movement of said sealing piston as far as the distal end of said locking spring, and, after distal movement of said plunger rod to expel said medication, a second proximal movement of said plunger rod is prevented by frictional engagement between said contact point and said interior cylindrical sidewall.

2. A single-use syringe as claimed in claim 1 wherein the distance between the longitudinal axis of said locking spring and said contact point of said locking spring, when said locking spring is removed from said plunger rod, is slightly greater than the radius of said interior cylindrical sidewall.

3. A single-use syringe as claimed in claim 1 wherein said plunger rod is provided with sealing means to prevent unauthorized access to said ratchet teeth and said locking spring.

4. A single-use syringe as claimed in claim 1 wherein sealing means are provided at both the distal end and the proximal end of said plunger rod to prevent unauthorized access to said ratchet teeth and said locking spring.

5. A single use syringe as claimed in claim 1 wherein said locking ring is a hollow open-ended hexagon and the spacing of said open end is less than the diameter of the base of said ratchet teeth.

6. A single-use syringe as claimed in claim 1 wherein the distance between said tab of said locking spring and said longitudinal axis, when said locking spring is mounted on said plunger rod, is less than the radius of the base of said ratchet teeth.

7. A single-use syringe as claimed in claim 1 wherein said plunger rod is provided with a thumb-contacting disk which is intended to be broken apart from said plunger rod after said single-use.

8. A single-use syringe as claimed in claim 1 wherein said plunger rod is provided with a thumb-contacting disk of a dove tail circumferential configuration and said barrel, at its proximal end is provided with a female dove tail opening, configured to mate with said dove tail circumferential configuration of said thumb-contacting disk and to cooperate and lock together such that full distal movement of said plunger rod with respect to said barrel locks said plunger within said barrel.

9. A single-use syringe as claimed in claim 1 wherein a pair of contact points are provided on both sides of said tab.

10. A single-use syringe as claimed in claim 1 wherein said tab cams over said ratchet teeth when said plunger rod is proximally moved with respect to said barrel.

11. A single-use syringe as claimed in claim 1 wherein said ratchet teeth are marked with dosage indicating means.

12. A single-use syringe as claimed in claim 1 wherein said locking spring is a single thickness of sheet metal.

13. A single-use syringe as claimed in claim 1 wherein said locking spring comprises an open ended hexagonal shape with said opening being less than the diameter of the base of said ratchet teeth.

14. A single-use syringe as claimed in claim 1 wherein said tab is centrally located on said locking spring and opposed pairs of contact points are located on both sides of said tab.

15. A single-use syringe as claimed in claim 1 wherein the dosage of said syringe is limited by the distance said piston may travel until it contacts the bottom edge of said locking spring.

16. A single use syringe as claimed in claim 1 wherein said thumb contacting disc is provided with inventory tracking means.

17. A set for ensuring single use of a conventional syringe of the hollow barrel type having an interior cylindrical sidewall, a hub for a needle tip at the distal end of the barrel and a proximal end opposite the hub for a needle tip of the barrel, said set comprising:

a plunger rod having a longitudinal axis to be located within the barrel for axial movement therein for drawing fluid into and expelling fluid out of the barrel through the needle tip, said plunger rod for extending beyond the barrel at the proximal end of the barrel when inserted therein, said plunger rod having a sealing piston at the distal end of said plunger rod;

said plunger rod being comprised of two or more frusto conical ratchet teeth extending along said longitudinal axis; and an open-ended resilient locking spring, locatable on any one of said ratchet teeth, said locking spring extending around the circumference of said plunger rod by more than 180 degrees but less than 360 degrees, said locking spring having at least one inwardly directed, ratchet tooth-engaging tab and at least one, outwardly-directed sidewall contact point;

said plunger rod being free to move a first time toward the proximal end of the barrel, said tab camming over the surface of said ratchet teeth as said plunger rod moves proximally while said locking spring is held in position by the frictional engagement of said contact point against—the interior cylindrical sidewall of the barrel and, yet, distal movement of said plunger rod causes said tab to engage the base of one of said ratchet teeth such that said locking spring moves along with said plunger rod in said distal direction;

whereby said locking spring permits the syringe to be loaded with medication in the volume of the barrel defined by a predetermined location of said locking spring on said plunger rod and by proximal movement of said sealing piston as far as the distal end of said locking spring, and, after distal movement of said plunger rod to expel said medication, a second proximal movement of said plunger rod is prevented by frictional engagement between said contact point and the interior cylindrical sidewall.

* * * * *